(12) United States Patent
Liu et al.

(10) Patent No.: US 8,290,232 B2
(45) Date of Patent: Oct. 16, 2012

(54) SYSTEM AND METHOD FOR QUANTITATIVE IMAGING OF CHEMICAL COMPOSITION TO DECOMPOSE MORE THAN TWO MATERIALS

(75) Inventors: Xin Liu, Rochester, MN (US); Lifeng Yu, Rochester, MN (US); Cynthia H. McCollough, Byron, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 739 days.

(21) Appl. No.: 12/371,425

(22) Filed: Feb. 13, 2009

(65) Prior Publication Data

US 2009/0208084 A1    Aug. 20, 2009

Related U.S. Application Data

(60) Provisional application No. 61/029,125, filed on Feb. 15, 2008.

(51) Int. Cl.
*G06K 9/00* (2006.01)
(52) U.S. Cl. ....................................................... 382/131
(58) Field of Classification Search .................. 382/128, 382/130–132; 378/4, 5, 19, 53, 54, 57, 64, 378/62
See application file for complete search history.

(56) References Cited

U.S. PATENT DOCUMENTS

| | | | |
|---|---|---|---|
| 4,029,963 | A | 6/1977 | Alvarez et al. |
| 5,235,628 | A | 8/1993 | Kalender |
| 6,987,833 | B2 | 1/2006 | Du et al. |
| 7,050,530 | B2 | 5/2006 | Heismann |
| 7,158,611 | B2 | 1/2007 | Heismann et al. |

OTHER PUBLICATIONS

Werner J. Glantschnig and Albert Holliday, Mass fraction profiling based on x-ray tomography and its application to characterizing porous silica boules, Mar. 15, 1987, Applied Optics, vol. 26, No. 6, pp. 983-989.*

* cited by examiner

*Primary Examiner* — Georgia Y Epps
*Assistant Examiner* — Renee Naphas
(74) *Attorney, Agent, or Firm* — Quarles & Brady, LLP

(57) ABSTRACT

A system and method for decomposing more than two materials in an imaging object includes performing a CT imaging acquisition of a portion of an imaging object using at least two energy levels to acquire imaging data associated with each of the at least two energy levels. A total mass attenuation of the imaging data is expressed as a weighted sum of constituent element mass attenuation coefficients and an effective atomic number and density of the constituent elements in the portion of the imaging object is determined by one of a number of methods. Accordingly, concentration of the constituent elements in imaged object is determined by solve the expression using known material attenuation coefficients and the measured CT data.

23 Claims, 3 Drawing Sheets

SYSTEM AND METHOD FOR QUANTITATIVE IMAGING OF CHEMICAL COMPOSITION TO DECOMPOSE MORE THAN TWO MATERIALS

CROSS-REFERENCE TO RELATED APPLICATIONS

This application is based on, incorporates herein by reference, and claims the benefit of U.S. Provisional Application 61/029,125, filed Feb. 15, 2008, and entitled "SYSTEM AND METHOD FOR QUANTITATIVE IMAGING OF CHEMICAL COMPOSITION TO DECOMPOSE MORE THAN TWO MATERIALS."

BACKGROUND OF THE INVENTION

The field of the invention is quantitative imaging and material decomposition. More particularly, the invention relates to a method for determining the mass fractions of constituent components of an object using CT imaging and a post-reconstruction material-basis model.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

Dual source CT systems have two separate x-ray sources and associated detector arrays, which rotate together in the gantry during a scan. The x-ray sources may be operated at different energy levels to acquire two image data sets from which a low energy and a high energy image may be reconstructed.

Quantitative imaging using CT systems has experienced tremendous growth in recent years, in terms of both the basic technology and new clinical applications. CT-based quantitative imaging exploits differences in x-ray attenuation between different materials. In CT images, because different materials cause different levels of x-ray scattering and absorption, proper calibration of image pixel values versus x-ray beam energy can be used to qualitatively and quantitatively evaluate an imaged object's material composition.

The degree to which a given material blocks x-ray transmission, is measured by an attenuation coefficient, which accounts for both energy absorption and the scattering of photons. Often, mass attenuation coefficients, which measure attenuation per unit mass, are utilized, because they do not change with the density of the material. Tabulated mass attenuation coefficients for different elements ($Z=1\sim92$) are readily available in the database of the National Institute of Standards and Technology (NIST). The NIST database also includes 48 compounds and mixtures, covering nearly all tissues found in the human body. The mass attenuation coefficient for compounds and mixtures having than more than one material is simply the summation of weighted mass attenuation coefficients of each constituent material, wherein the weighting factor is the mass fraction of each constituent material. Material decomposition techniques can be employed to calculate these mass fractions using known mass attenuation coefficients and dual energy CT measurements. In principle, this can only be done for objects having two constituent materials, as dual energy CT provides only two independent measurements.

Alternatively, material decomposition techniques can quantify and object under investigation by analyzing the physical mechanisms that cause attenuation. For the x-ray energies in the medical diagnostic range, the mechanisms responsible for material attenuation are the photoelectric effect and Compton scattering, which can be approximately modeled using effective atomic number, density, and x-ray energy information. Therefore, instead of obtaining the mass fraction of each material, the effective atomic number and density of the imaged object can be determined using a model of these two mechanisms and dual energy CT measurements.

In 1976, Alvarez and Macovski proposed a method to couple the attenuation coefficient model with CT measurements in order to determine the atomic number and density of a material. First, the attenuation coefficient ($\mu(\ldots)$) is modeled as a linear combination of the photoelectric effect and Compton scattering, as follows:

$$\mu(x, y, E) = a_1(x, y)\frac{1}{E^3} + a_2(x, y)f_{KN}(E). \quad \text{Eqn. 1}$$

In Eqn. 1, the photoelectric effect is inversely proportional to the energy level (E) cubed, and the Compton scattering is modeled by Klein-Nishina formula. The terms $a_1(x, y)$ and $a_2(x, y)$ are related to the atomic number and physical density of the materials under investigation. For a CT scan, this model is expressed as the following line integral:

$$\int \mu(x, y, E)ds = A_1\frac{1}{E^3} + A_2 f_{KN}(E); \quad \text{Eqn. 2}$$

where:

$$A_1 = \int a_1(x, y)ds; \quad \text{Eqn. 3}$$

and $$A_2 = \int a_2(x, y)ds. \quad \text{Eqn. 4}$$

From Eqn. 2, at least two equations are needed to obtain the single solution of the two unknowns. Because dual-energy CT images the object at two different energy levels, it satisfies this requirement and the equation can be written as follows:

$$I_i = \int S_i(E) e^{-\frac{A_1}{E^3} - A_2 f_{KN}(E)} dE \qquad \text{Eqn. 5}$$

$(i = 1, 2).$

However, it is very difficult to solve Eqn. 5 for $A_1$ and $A_2$. Alvarez and Macovski therefore used the following power series to approximate the integral equation:

$$\ln I_1 = b_0 + b_1 A_1 + b_2 A_2 + b_3 A_1^2 + b_4 A_2^2 + b_5 A_1 A_2 + b_6 A_1^3 + b_7 A_2^3 \qquad \text{Eqn. 6;}$$

and $$\ln I_2 = c_0 + c_1 A_1 + c_2 A_2 + c_3 A_1^2 + c_4 A_2^2 + c_5 A_1 A_2 + c_6 A_1^3 + c_7 A_2^3 \qquad \text{Eqn. 7.}$$

The sets of coefficients $\{b_i\}$ and $\{c_i\}$ are determined by calibrations. Once the $A_1$ and $A_2$ are solved using Eqn. 6 and 7, $a_1(x,y)$ and $a_2(x,y)$ can be reconstructed by one of the reconstruction methods, such as filtered back projection.

This method, typically referred to as the basis-spectral method, was the first theoretical analysis on material-selective imaging using dual-energy CT. The drawback of the basis-spectral method is that it is not very accurate due to the intrinsic difficulty in modeling the photoelectric effect and Compton scattering, especially for discontinuous absorption edges. Although the basis-spectral method accounts for the photoelectric effect and Compton scattering by creating a photoelectric effect and Compton scattering map, this type of technique is more often used to give the object's effective atomic number (Z) and density ($\rho$).

In 1986, Kalender et al. proposed that any material's mass attenuation coefficient can be expressed as a linear combination of the coefficients of two so-called basis materials, as follows:

$$\left(\frac{\mu}{\rho}\right)(E) = a_1 \left(\frac{\mu}{\rho}\right)_1 (E) + a_2 \left(\frac{\mu}{\rho}\right)_2 (E). \qquad \text{Eqn. 8}$$

For a CT measurement, this is expressed using the following line integral:

$$\int \mu(x, y, E) ds = A_1 \left(\frac{\mu}{\rho}\right)_1 (E) + A_2 \left(\frac{\mu}{\rho}\right)_2 (E); \qquad \text{Eqn. 9}$$

where $$A_1 = \int \rho_1(x, y) ds; \qquad \text{Eqn. 10}$$

and $$A_2 = \int \rho_2(x, y) ds. \qquad \text{Eqn. 11}$$

This method is called the basis-material method. Similar to the basis-spectral method, dual-energy CT measurements are needed to solve the two unknowns $A_1$ and $A_2$. The assumption used with the basis-material method is that the attenuation coefficients of the two basis materials are known. From this assumption and the dual-energy CT measurements, the line integral equation can be written as follows:

$$I_i = \int S_i(E) e^{\left[-A_1 \left(\frac{\mu}{\rho}\right)_1 (E) - A_2 \left(\frac{\mu}{\rho}\right)_2 (E)\right]} dE. \qquad \text{Eqn. 12}$$

Instead of solving Eqn. 12 directly, the basis-material method uses a table lookup procedure to solve the equation and produce an output that can be interpreted as components in a two-dimensional vector space, wherein the basis materials define the basis vectors. As a result, the basis-material method using dual energy CT is more efficient and clinically practical than the above-described basis-spectral approach.

Although the basis-spectral and basis-material methods differ in their modeling of the attenuation coefficients, they both belong to the "pre-reconstruction" class of methods. That is, both methods are performed with "raw data," prior to image reconstruction. In contrast, a post-reconstruction method would be capable of analyzing reconstructed images directly.

In 2003, Heismann et al. proposed a general post-reconstruction method for performing material decomposition using CT. Under the Heismann method, the effective attenuation coefficient is first defined as follows:

$$\mu_{eff} = \lim_{d \to 0} \left[-\frac{1}{d} \ln\left(\frac{I}{I_0}\right)\right] = \lim_{d \to 0} \left[-\frac{1}{d} \ln\left(\frac{\int S(E) D(E) e^{-\mu(E) d} dE}{\int S(E) D(E) dE}\right)\right]. \qquad \text{Eqn. 13}$$

Then, as follows:

$$\mu_{eff} = \int w(E) \mu(E) dE; \qquad \text{Eqn. 14}$$

where $$w(E) = \frac{S(E) D(E)}{\int S(E) D(E) dE}. \qquad \text{Eqn. 15}$$

The effective attenuation coefficient ($\mu_{eff}$) is determined from the CT image data and S(E) and D(E) are the tube spectrum and detector sensitivity, respectively. Like the basis-spectral method, the Heismann method treats $\mu(E)$ as the following linear combination of the photoelectric effect and Compton scattering:

$$\begin{pmatrix} \mu_{eff1} \\ \mu_{eff2} \end{pmatrix} = \rho \begin{pmatrix} \int w_1(E) \left(\frac{\mu_{photo}}{\rho} + \frac{\mu_{Compton}}{\rho}\right) dE \\ \int w_2(E) \left(\frac{\mu_{photo}}{\rho} + \frac{\mu_{Compton}}{\rho}\right) dE \end{pmatrix}. \qquad \text{Eqn. 16}$$

Again like the basis-spectral method, the Heismann method models the photoelectric effect and Compton scattering as functions of atomic number and x-ray energy, respectively, as follows:

$$\frac{\mu_{photo}}{\rho} = \alpha \frac{Z^3}{E^3}; \qquad \text{Eqn. 17}$$

and $$\frac{\mu_{Compton}}{\rho} = \beta; \qquad \text{Eqn. 18}$$

where α and β are constants. Therefore, Heismann's post-reconstruction method determines an object's effective atomic number and density directly from CT images. The Heismann method, though able to utilize CT data post-reconstruction, shares many of the assumptions of the above-described pre-reconstruction spectral-basis method. As a result, the Heismann method suffers from similar drawbacks.

Heismann did not determine how to use the data in both the pre-reconstruction space and post-reconstruction space, how to solve the linear equations more accurately, and other measures, such as the beam hardening effect, necessary to successfully implement such a method.

In addition, the above-described methods are incapable of performing three material decomposition using dual energy CT data. This can be problematic, as clinicians often encounter situations in which more than two materials coexist in an object, for example, when imaging bone, tissue, and an iodinated contrast material. In such cases, additional information is required because n>m. Therefore, three equations are theoretically needed to solve for three unknowns and perform three-material decomposition. Accordingly, one method for performing three-material decomposition includes employing triple-energy CT systems so that m=n. However, the mechanisms of photon attenuation are mainly the photoelectric effect and Compton scattering, triple-energy CT systems are not very useful.

A method for performing three-material decomposition using dual-energy CT data was proposed previously. The previous method assumes that the volume fraction of three materials in an imaged object can be expressed as follows:

$$f_1+f_2+f_3=1 \qquad \text{Eqn. 19;}$$

where $f_1$ to $f_3$ are the volume fractions as illustrated in FIG. 1, which depicts a three material object including a first material volume fraction $f_1$ having a known density $\rho_1$, a second material volume fraction $f_2$ having a known density $\rho_2$, and a third material volume fraction $f_3$ having a known density $\rho_3$. Therefore the effective density $\rho$ of the three material mixture can be expressed as follows:

$$\rho=f_1\rho_1+f_2\rho_2+(1-f_1-f_2)\rho_3 \qquad \text{Eqn. 20.}$$

Thus, the effective attenuation coefficient is as follows:

$$\mu=f_1\mu_1+f_2\mu_2+(1-f_1-f_2)\mu_3 \qquad \text{Eqn. 21;}$$

where $\mu_1$, $\mu_2$ and $\mu_3$ are the attenuation coefficients of the three materials, respectively. Accordingly, only two unknowns, $f_1$ and $f_2$, need to be solved to perform three material decomposition using dual energy CT data.

The volume-conservation three-material decomposition method works well in some cases, especially when the three materials are solid with clear boundaries between each other. However, there are many clinical situations where the three materials are not completely solid and lack clearly defined boundaries. The volume-conservation method is not applicable under these situations.

Accordingly, it would be desirable to have a system and method for performing three-material decomposition without the need for three-energy measurements. In addition, this system and method should provide more accurate and widely applicable clinical data than the volume-conservation method.

SUMMARY OF THE INVENTION

The present invention overcomes the aforementioned drawbacks by enabling the decomposition of more than two constituent materials using dual energy CT data in a more precise manner than previous methods. The present invention first uses traditional dual energy CT measurements to determine the density of an imaged object. The density information and the dual energy CT measurements are then used to determine the constituent material concentration in the imaged object. More specifically, the determined concentration is in the form of mass fraction, mass percent, weight fraction, or weight percent. This form of concentration measurement provides significantly improved accuracy over the volume fraction measurements, especially when imaging dense materials occupying small portions of the imaged object.

In accordance with one aspect of the invention, a method for performing material decomposition using a CT system is disclosed that includes imaging an object with a CT system using at least two different energy levels to acquire CT data associated with each of the energy levels. The method also includes expressing a total mass attenuation of an object as a weighted sum of constituent material mass attenuation coefficients and determining an effective density of the imaged object. The method then includes indicating a concentration of the constituent materials from the acquired CT data and the determined density using the expression of total mass attenuation. The concentration includes a mass fraction, mass percent, weight fraction, or weight percent.

In accordance with another aspect of the invention, a method for performing material decomposition using a CT system is disclosed that includes imaging an object with the CT system using at least two different energy levels to acquire CT data associated with each energy level and reconstructing the CT data to produce CT images associated with each of the energy levels. Thereafter, the CT images are converted to mass attenuation coefficients associated with each energy level and an effective density of the imaged object is determined from the acquired CT data associated with each energy level or the CT images associated with each energy level. The method also includes expressing the mass attenuation coefficients associated with each energy level as the product of the determined effective density and a sum of constituent materials mass attenuation coefficients weighted by respective concentrations of the constituent materials, including a mass fraction, mass percent, weight fraction, or weight percent. Accordingly, an indication of the concentrations of the constituent materials can be provided.

Various other features of the present invention will be made apparent from the following detailed description and the drawings.

DETAILED DESCRIPTION OF THE INVENTION

Figure 1:
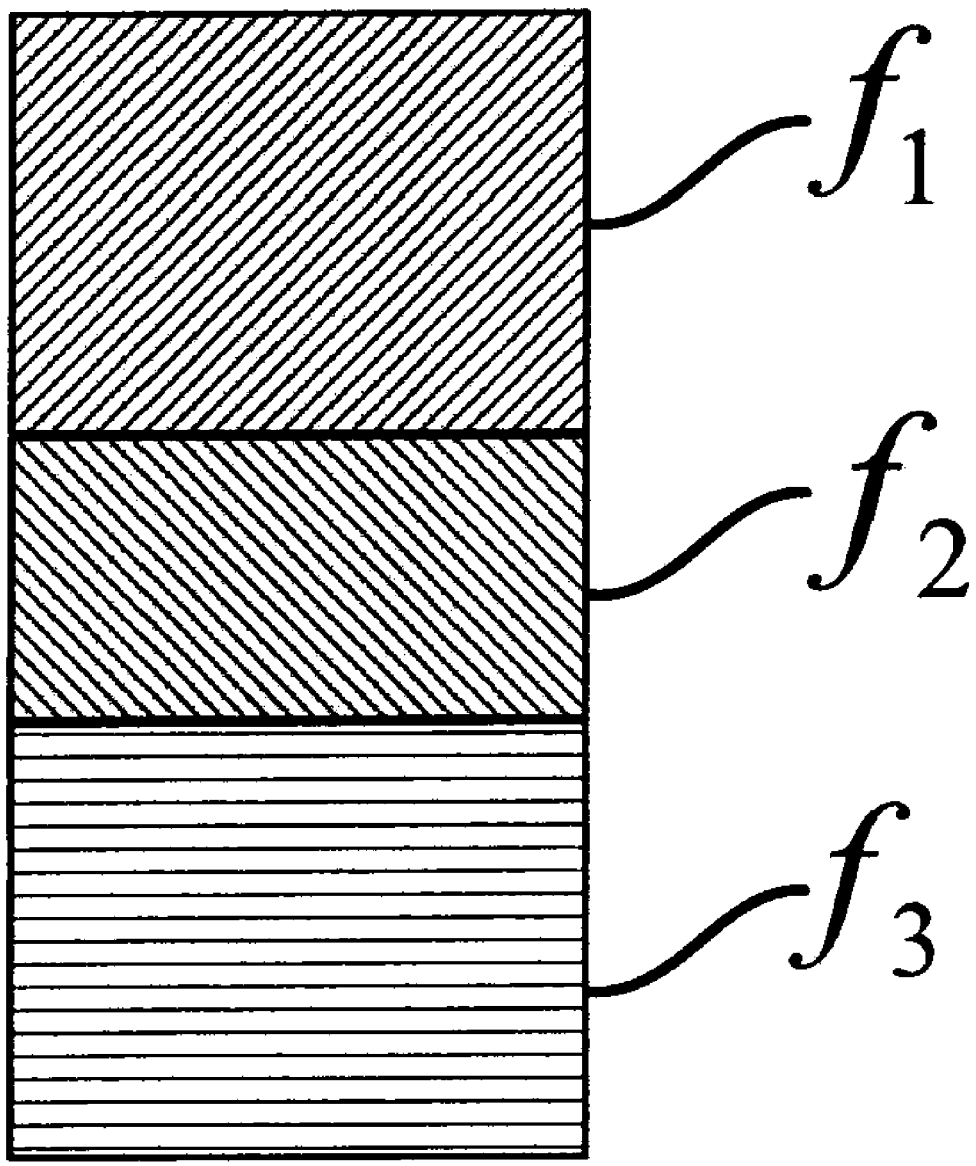
FIG. 1 is a schematic depiction of three-material object including three material volume fractions.
Figure 2:
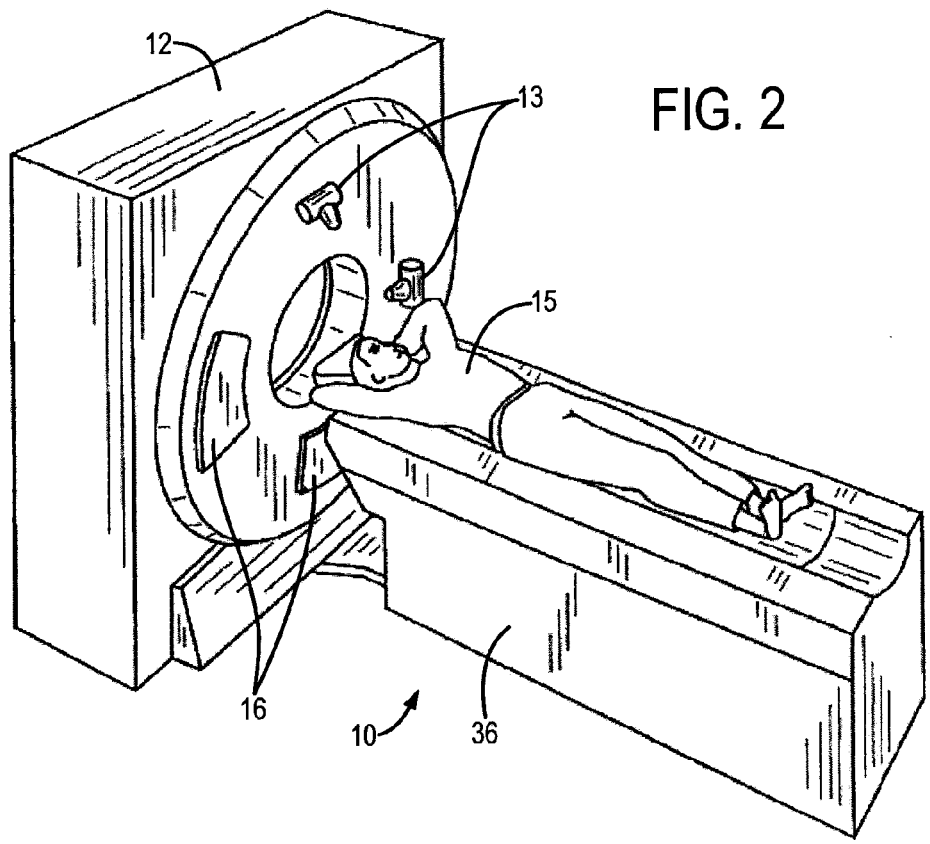
FIG. 2 is pictorial view of a CT imaging system in which the present invention may be employed.
Figure 3:
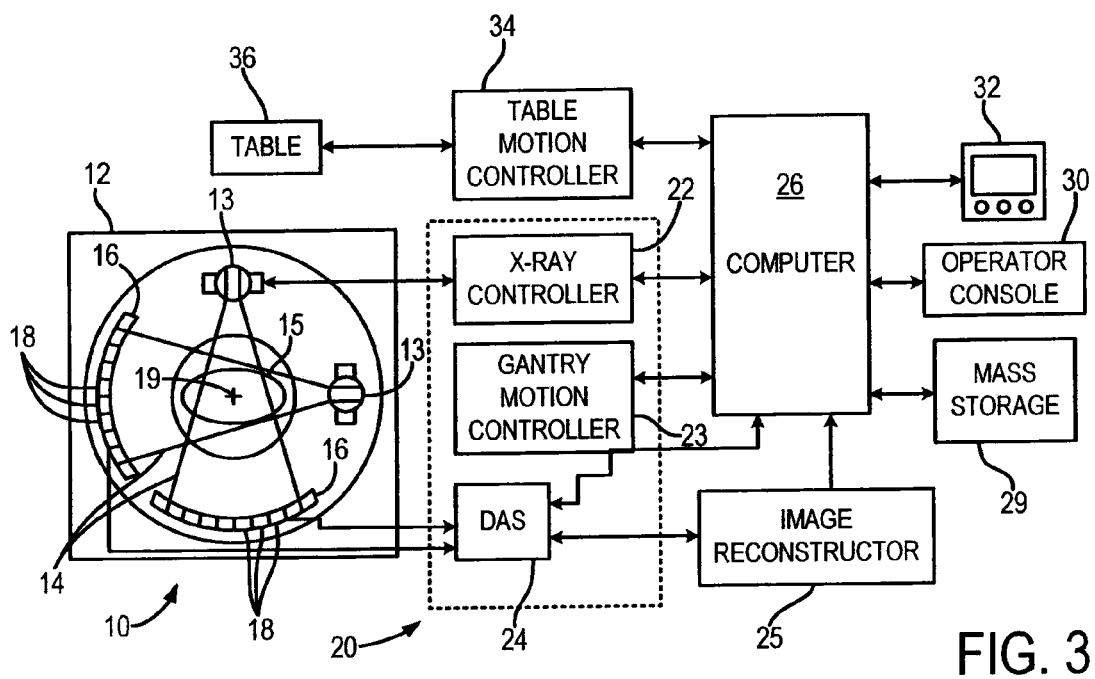
FIG. 3 is block schematic diagram of the CT imaging system of FIG. 2.

With initial reference to FIGS. 2 and 3, a computed tomography (CT) imaging system 10 includes a gantry 12 representative of a "third generation" CT scanner. Gantry 12 has a pair of x-ray sources 13 that each project a fan beam or cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15 to acquire attenuation data for each of the two x-ray sources.

The rotation of the gantry and the operation of the x-ray sources 13 are governed by a control mechanism 20 of the CT system. The control mechanism 20 includes an x-ray controller 22 that provides power and timing signals to the x-ray sources 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

The above-described third generation CT system may be operated in a dual energy mode while performing a scan. More particularly, at each view angle the x-ray controller 22 operates the x-ray tube 13 to acquire both a low energy transmission profile and a high energy transmission profile. This is accomplished by switching the anode voltage on the x-ray tube between two levels that produce the prescribed x-ray energy levels. The transmission profile views for each energy level are separately stored and processed as described in more detail below.

The above-described CT system may be employed to perform post-reconstruction three-material decomposition using dual energy CT data and provide density and concentration information for the constituent materials of an imaged object. However, before describing the three-material decomposition method of the present invention, it is advantageous to define the three-material decomposition problem. Specifically, the object under study is a mixture of three constituent materials with known properties such as bone, fat, and tissue, wherein the concentration, effective atomic number, and density of each constituent material is unknown. As mentioned above, the mass attenuation coefficient of such a mixture having more than one constituent element can be modeled as a weighted sum of the mass attenuation coefficients of the constituent materials.

Figure 4:
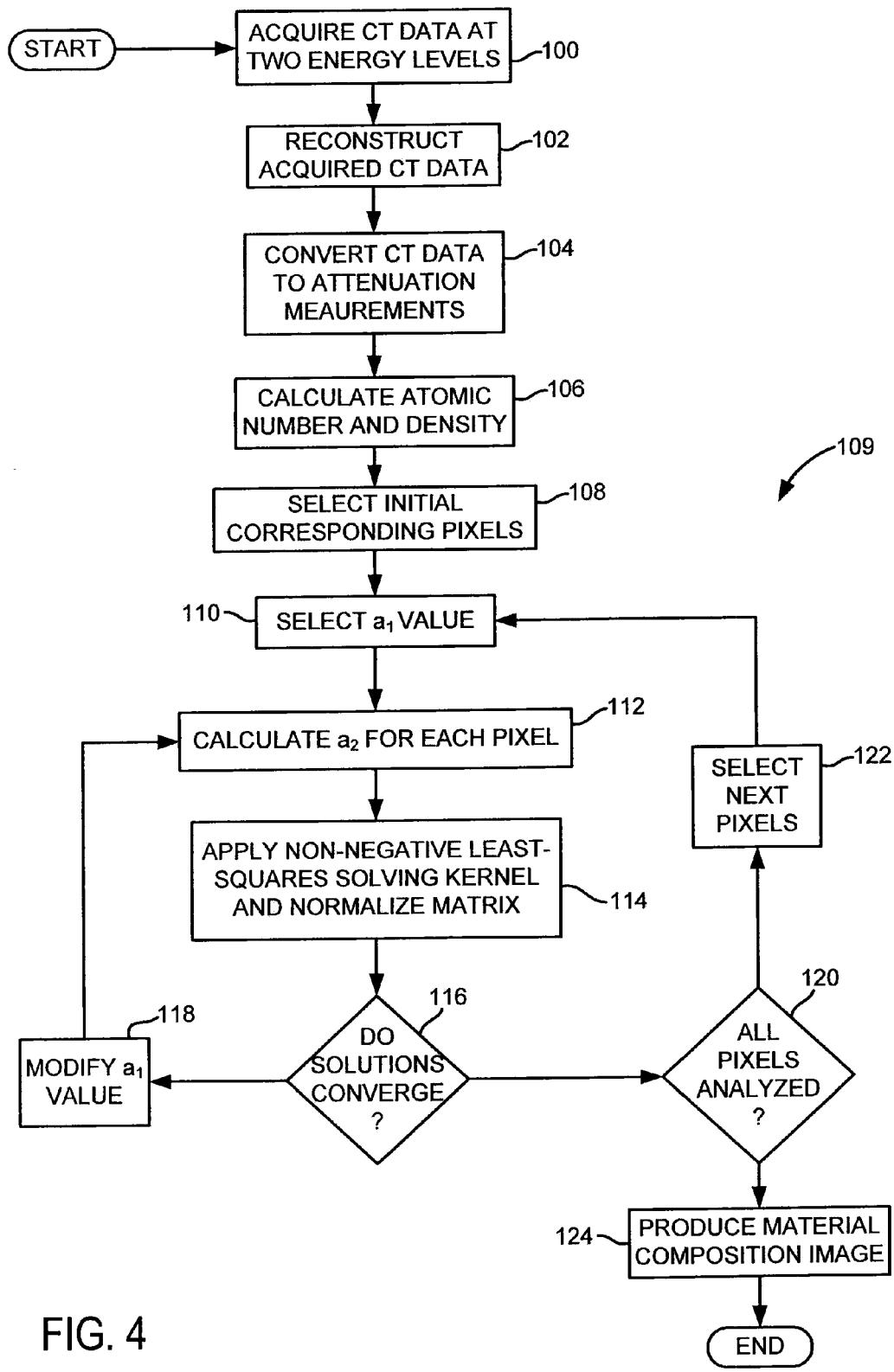
FIG. 4 is a flowchart setting forth the steps of performing three-material decomposition in accordance with the present invention.

Referring to FIG. 4, with this perspective, a three-material decomposition method in accordance with the present invention begins at process block 100 with the acquisition of CT data from an object at two energy levels. For example, a dual energy CT system may be used to acquire CT data from an object containing tissue, bone, and iodinated contrast agent at 80 kVp and 120 kVp. The acquired CT data is then reconstructed at process block 102 to produce CT images associated with each energy level. For the above-noted dual energy CT scan, for example, filtered backprojection may be employed to produce CT images associated with the 80 kVp scan and CT images associated with the 120 kVP scan. At process block 104, the reconstructed CT images are processed so that the CT number in Hounsfield Units (HU) at each pixel is converted to attenuation coefficient.

At process block 106, the effective atomic numbers and densities, Z and ρ respectively, are calculated for each corresponding pixel of the CT images using one of the above-described spectral-basis methods. It should be noted that Z and ρ may alternately be calculated prior to image reconstruction using an appropriate method. The total attenuation coefficient of the imaged object may be expressed as the weighted sum of the attenuation coefficient of its constituent materials using the following equation:

$$\left(\frac{\mu}{\rho}\right)(E) = a_1\left(\frac{\mu}{\rho}(E)\right)_1 + a_2\left(\frac{\mu}{\rho}(E)\right)_2 + (1 - a_1 - a_2)\left(\frac{\mu}{\rho}(E)\right)_3; \quad \text{Eqn. 22}$$

where $a_1$, $a_2$, and $(1-a_1-a_2)$ are the concentrations of the first, second, and third constituent materials respectively. It should be noted that these concentrations can be weight percents, weight fractions, mass percents, mass fractions, or other appropriate measurements of concentration and that the mass attenuation coefficients of these constituent materials are known. The above model can be expanded to perform three-material decomposition using dual energy CT data as follows:

$$\begin{pmatrix}\mu_{\mathit{eff}1}\\ \mu_{\mathit{eff}2}\end{pmatrix} = \rho_{\mathit{eff}}\begin{pmatrix}\left(\int w_1(E)\left[a_1\left(\frac{\mu}{\rho}(E)\right)_1 + a_2\left(\frac{\mu}{\rho}(E)\right)_2 + (1-a_1-a_2)\left(\frac{\mu}{\rho}(E)\right)_3\right]dE\right)\\ \left(\int w_2(E)\left[a_1\left(\frac{\mu}{\rho}(E)\right)_1 + a_2\left(\frac{\mu}{\rho}(E)\right)_2 + (1-a_1-a_2)\left(\frac{\mu}{\rho}(E)\right)_3\right]dE\right)\end{pmatrix}; \quad \text{Eqn. 23}$$

where the effective density $\rho_{\mathit{eff}}$ is the density measurement calculated at process block 106. Therefore, as indicated generally by loop 109, a dual energy dataset can be employed to solve Eqn. 23 for the unknowns $a_1$ and $a_2$ for corresponding pixels of the CT images. For example, in the above-noted dual energy CT scan, the attenuation coefficients associated with the 80 kVp and 120 kVp scans, that is, $\mu_{\mathit{eff}1}$ and $\mu_{\mathit{eff}2}$, may be employed to determine the mass fractions of the bone, tissue, and contrast agent constituents, that is, $a_1$, $a_2$, and $(1-a_1-a_2)$, at corresponding pixels.

However, because image noise often makes it difficult to solve Eqn 23 directly, the present invention provides a method of determining $a_1$ and $a_2$ using a least-squares fitting and an iteration scheme. Specifically the low-energy equation in Eqn. 23 is expanded as follows:

$$\frac{\mu_{\mathit{eff}2}}{\rho_{\mathit{eff}}} = a_1\int w_2(E)\left[\left(\frac{\mu}{\rho}(E)\right)_1 - \left(\frac{\mu}{\rho}(E)\right)_3\right]dE + \quad \text{Eqn. 24}$$
$$a_2\int w_2(E)\left[\left(\frac{\mu}{\rho}(E)\right)_2 - \left(\frac{\mu}{\rho}(E)\right)_3\right]dE + \int w_2(E)\left(\frac{\mu}{\rho}(E)\right)_3 dE.$$

-continued $$a_2 = \frac{\frac{\mu_{eff2}}{\rho_{eff}} - \int w_2(E)\left(\frac{\mu}{\rho}(E)\right)_3 dE - a_1 \int w_2(E)\left[\left(\frac{\mu}{\rho}(E)\right)_1 - \left(\frac{\mu}{\rho}(E)\right)_3(E)\right]dE}{\int w_2(E)\left[\left(\frac{\mu}{\rho}(E)\right)_2 - \left(\frac{\mu}{\rho}(E)\right)_3(E)\right]dE}.$$ Eqn. 25

At process block 108, the iteration scheme begins by selecting corresponding pixels of the CT images associated with each energy level. Because of the conversion performed at process block 104, this step effectively selects an attenuation coefficient from the low energy scan and the corresponding attenuation coefficient from the high energy scan. For example, this may include selecting the attenuation coefficient at pixel($i_1, j_1$) of an 80 kVp image and the attenuation coefficient at pixel($i_1, j_1$) of a 120 kVp image. For the selected pixels, an initial concentration value $a_1$ is assigned at process block 110 and, at process block 112, a concentration $a_2$ is calculated from the initial concentration $a_1$ using Eqn. 25. A non-negative least-squares solving kernel and a normalization technique are subsequently used at process block 114 to solve the linear equations of Eqn. 24 for $a_1$ and $a_2$. The solution is then checked for convergence at decision block 116. If the solution does not meet specified convergence criteria after a maximum number of iterations, then the initial concentration $a_1$ is modified at process block 118 and the calculations steps of process blocks 112 and 114 are repeated. If, at decision block 120, all corresponding pixels of the CT images have not been analyzed, then another set of corresponding pixels is selected at process block 122, and the steps of process blocks 112 to 118 are repeated.

When all corresponding pixels have been analyzed, at process block 124, a material composition image showing the distribution of constituent material concentrations throughout the imaged object is produced from the determined values of $a_1$, $a_1$, and $a_3$. The material composition image shows the distribution of constituent material concentration throughout the imaged object. For example, a material composition image produced from a dual energy CT scan could show the distribution of up to three constituent material concentrations.

Specifically, the image will show the distribution of the mass fractions, mass percents, weight fractions, or weight percents of the constituent materials throughout the imaged object. An image showing the distribution of these measurements of concentration will generally provide higher clinical accuracy than an image showing the distribution of the constituent materials' volume fractions, that is, images produced using the volume-conservation method. Because material attenuation is proportional to material density, high density materials occupying small portions of the imaged object can have a strong effect total attenuation coefficient of the object. However, because they occupy a small volume, and therefore have a small volume fraction, the effects of these small, high-density materials is underrepresented by the volume-conservation method. For example, in a hemachromatosis case, the iron molecule occupies a very small volume portion of the imaged object and, as a result, has small volume fraction that may easily be neglected by the volume-conservation method. However, the mass fraction of iron in such a case would be significantly larger than the volume fraction. Accordingly, the present invention more accurately accounts for the iron's effect on the total attenuation coefficient of the imaged object and thus generates an image that more accurately shows the distribution of iron within the imaged object.

It should be noted that the above method can be utilized with dual-energy, single-source CT systems; dual-source, dual-energy CT systems; or any other CT system capable of acquiring multi-energy data. For example, so-called "photon counting" and "energy discriminating" CT systems can also be employed. In such systems, one spectrum is measured and divided into two energy bands.

The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

The invention claimed is:

1. A method for performing material decomposition using a CT system, the method comprising:
   a) imaging an object with a CT system using at least two different energy levels to acquire CT data associated with each of the energy levels;
   a)i) reconstructing the CT data associated with each energy level to produce CT images associated with each energy level;
   a)ii) converting the CT images associated with each energy level to produce attenuation coefficients associated with each energy level;
   b) expressing a total mass attenuation of the object as a weighted sum of constituent material mass attenuation coefficients;
   c) determining an effective density of the imaged object;
   d) determining concentrations of the constituent materials from the attenuation coefficients associated with each energy level determined at step a)ii) and the effective density determined in step c) using the expression of step b),
   wherein said determining concentrations includes employing an iterative least-squares technique,
   wherein a concentration is at least one of a mass fraction, mass percent, weight fraction, and weight percent; and
   e) producing an image using the CT data and the concentrations of the constituent materials illustrating the distribution of the concentrations of the constituent materials within the object.

2. The method as recited in claim 1 wherein step d) includes:
   d) i) estimating a concentration of a second constituent material from an estimated concentration of a first constituent material using a portion of the expression of step b);
   d) ii) producing estimated mass attenuation coefficients associated with each energy level from the estimated concentrations of the first and second constituent materials using the expression of step b);
   d) iii) determining a difference between the estimated mass attenuation coefficients associated with each energy level and the mass attenuation coefficients associated with each energy level;
   d) iv) repeating steps d) i) to d) iii) until the difference between the estimated mass attenuation coefficients associated with each energy level and the mass attenuation coefficients associated with each energy level reaches a desired threshold to determine the concentrations of the constituent materials.

3. The method as recited in claim 1, wherein the CT system is a dual energy CT system, wherein the imaged object includes three constituent materials, and wherein the concentrations of the three constituent materials are indicated at step d).

4. The method as recited in claim 1, wherein step c) further includes determining an effective atomic number of the imaged object.

5. The method as recited in claim 4, wherein the effective density and atomic number of the imaged object are determined using a basis-spectral method.

6. The method as recited in claim 1, wherein the CT system includes at least one of a photon counting CT system and an energy discriminating CT system.

7. A method for performing material decomposition using a CT system, the method comprising:
   a) imaging an object with a CT system using at least two different energy levels to acquire CT data associated with each of the energy levels;
   b) expressing a total mass attenuation of the object as a weighted sum of constituent material mass attenuation coefficients;
   c) determining an effective density of the imaged object including determining an effective atomic number of the imaged object; and
   d) indicating concentrations of the constituent materials from the data acquired in step a) and the density determined in step c) using the expression of step b), wherein a concentration is at least one of a mass fraction, mass percent, weight fraction, and weight percent.

8. The method as recited in claim 7 further including step e) producing an image using the CT data and the concentrations of the constituent materials illustrating the distribution of the concentrations of the constituent materials within the object.

9. The method as recited in claim 8 further including:
   a) i) reconstructing the CT data associated with each energy level to produce CT images associated with each energy level; and
   a) ii) converting the CT images associated with each energy level to produce attenuation coefficients associated with each energy level.

10. The method as recited in claim 9 wherein step d) includes determining the concentrations of the constituent materials from the attenuation coefficients associated with each energy level and the density determined in step c) using the expression of step b).

11. The method as recited in claim 10 wherein step d) includes employing an iterative least-squares technique to determine the concentrations of the constituent materials.

12. The method as recited in claim 11 wherein step d) includes:
   d) i) estimating a concentration of a second constituent material from an estimated concentration of a first constituent material using a portion of the expression of step b);
   d) ii) producing estimated mass attenuation coefficients associated with each energy level from the estimated concentrations of the first and second constituent materials using the expression of step b);
   d) iii) determining a difference between the estimated mass attenuation coefficients associated with each energy level and the mass attenuation coefficients associated with each energy level;
   d) iv) repeating steps d) i) to d) iii) until the difference between the estimated mass attenuation coefficients associated with each energy level and the mass attenuation coefficients associated with each energy level reaches a desired threshold to determine the concentrations of the constituent materials.

13. The method as recited in claim 7 wherein the CT system is a dual energy CT system, wherein the imaged object includes three constituent materials, and wherein the concentrations of the three constituent materials are indicated at step d).

14. The method as recited in claim 7 wherein the effective density and atomic number of the imaged object are determined using a basis-spectral method.

15. A method for performing material decomposition using a CT system, the method comprising:
   a) imaging an object with the CT system using at least two different energy levels to acquire CT data associated with each energy level;
   b) reconstructing the CT data to produce CT images associated with each of the energy levels;
   c) converting the CT images to mass attenuation coefficients associated with each energy level;
   d) determining an effective density of the imaged object from at least one of the acquired CT data associated with each energy level and the CT images associated with each energy level;
   e) expressing the mass attenuation coefficients associated with each energy level as the product of the effective density determined in step d) and a sum of constituent materials mass attenuation coefficients weighted by respective concentrations of the constituent materials, wherein the concentrations are at least one of a mass fraction, mass percent, weight fraction, and weight percent; and
   f) providing an indication of the concentrations of the constituent materials using the expression of step e), wherein providing an indication includes employing an iterative, non-negative least squares technique to indicate the concentrations of the constituent materials.

16. The method as recited in claim 15 further including step g) producing an image showing the distributions of the concentrations of the constituent materials using CT images and the concentrations provided in step d).

17. The method as recited in claim 15 wherein step f) further includes:
   f) i) estimating a concentration of the second constituent material from an estimated concentration of the first constituent material using a portion of the expression of step e);
   f) ii) estimating attenuation coefficients associated with each energy level from the estimated concentrations of the first and second constituent materials using the expression of step e);
   f) iii) determining a difference between the estimated attenuation coefficients and the mass attenuation coefficients associated with each energy level; and
   f) iv) repeating steps f) i) to f) iii) until the difference between the estimated attenuation coefficients associated with each energy level and the mass attenuation coefficients associated with each energy level reaches a desired threshold to indicate the concentrations of the first and second constituent materials.

18. The method as recited in claim 17 further including step f)v) indicating a concentration of a third constituent material by subtracting the concentrations of the first and second constituent materials from one.

19. The method as recited in claim 15 wherein the CT system is a dual energy system and the imaged object includes three constituent materials.

20. The method as recited in claim 19 wherein:
   step a) includes imaging the object a high energy level and a low energy level using the dual energy CT system to acquire CT data associated with the high energy level and CT data associated with the low energy level;

step b) includes reconstructing the acquired CT data produce CT images associated with the high energy level and CT images associated with the low energy level;

step c) includes converting the CT images to produce attenuation coefficients associated with the high energy level and mass attenuation coefficients associated with the low energy level;

step e) includes expressing the attenuation coefficients associated with the high energy level and the attenuation coefficients associated with the low energy level as the effective density determined in step d) times the sum of the mass attenuation coefficients of the first, second, and third constituent materials weighted by the concentrations of the first and second constituent materials; and step f) includes i) indicating the concentrations of the first and second constituent materials using the expression of step e) and ii) determining the concentration of the third constituent material by subtracting the concentrations of the first and second constituent materials from one.

21. The method as recited in claim 20 wherein step f) i) includes employing an iterative non-negative least squares technique to determine the concentrations of the first and second constituent materials.

22. The method as recited in claim 15 wherein the effective density of the imaged object is determined using a basis-spectral method.

23. The method as recited in claim 15 wherein the CT system is at least one of a photon counting CT system and a energy discriminating CT system.

* * * * *